United States Patent
Ghatak et al.

(10) Patent No.: US 9,869,596 B2
(45) Date of Patent: Jan. 16, 2018

(54) NON-CONTACT METHOD FOR MEASUREMENT OF STRAIN PROFILE AT A LOCATION INTERPOSED WITHIN A SOFT DEFORMABLE OBJECT WITH DYNAMIC EVOLUTION OF THE STRAIN UNDER DYNAMIC LOADING OR FRACTURE OF THE OBJECT

(71) Applicants: Indian Council of Medical Research, New Delhi (IN); Indian Institute of Technology, Kanpur (IN)

(72) Inventors: Animangsu Ghatak, Kanpur (IN); Susmita Das, Kanpur (IN); Sukumar Laha, Kanpur (IN)

(73) Assignees: Indian Council of Medical Research, New Delhi; Indian Institute of Technology, Uttar Pradesh ( * ) Notice: Subject to any disclaimer, the term of this patent is extended or adjusted under 35 U.S.C. 154(b) by 164 days.

(21) Appl. No.: 14/888,211

(22) PCT Filed: Apr. 28, 2014

(86) PCT No.: PCT/IN2014/000283
§ 371 (c)(1),
(2) Date: Oct. 30, 2015

(87) PCT Pub. No.: WO2014/178080
PCT Pub. Date: Nov. 6, 2014

(65) Prior Publication Data
US 2016/0069757 A1    Mar. 10, 2016

(30) Foreign Application Priority Data
May 3, 2013  (IN) ............................ 1305/DEL/2013

(51) Int. Cl.
*G01L 1/24* (2006.01)
*G01B 11/16* (2006.01)
*A61B 5/00* (2006.01)

(52) U.S. Cl.
CPC .............. *G01L 1/24* (2013.01); *G01B 11/165* (2013.01); *G01L 1/247* (2013.01); *A61B 5/442* (2013.01)

(58) Field of Classification Search
CPC ................................ G01L 1/241; G01L 1/247
See application file for complete search history.

(56) References Cited

U.S. PATENT DOCUMENTS 4,288,852 A * 9/1981 Holland ............... G01B 11/024
                                                    382/152
4,781,455 A   11/1988 Machler et al.
(Continued)

FOREIGN PATENT DOCUMENTS

EP      0783837 B1    4/2002
EP      1281070 A1    2/2003
(Continued)

*Primary Examiner* — Lisa Caputo
*Assistant Examiner* — Tran M Tran
(74) *Attorney, Agent, or Firm* — The Webb Law Firm (57) ABSTRACT

A non-invasive method for estimation of strain profile and dynamic evolution of the strain at a location interposed inside a block of soft material, includes forming a tracer grid consisting of microscopic lines or regularly spaced microscopic dots on a single plane buried inside the soft block; preparation of a deformable object embedded with the tracer grid in three primary steps: i. preparing a block of cross-linked material by crosslinking a first predetermined quantity of a pre-polymer solution containing a monomer, a crosslinking agent, and an initiator and promoter all mixed in a solvent at a known stoichiometric weight ratio; ii. transferring a grid comprising of lines or dots onto the face by direct writing or transferring from an easy release sur- (Continued)

face; and iii. crosslinking a second predetermined quantity of the same pre-polymer solution on the gel surface, such that this second crosslinked material gets welded to the first one.

9 Claims, 10 Drawing Sheets

(56) References Cited

U.S. PATENT DOCUMENTS

| | | | |
|---|---|---|---|
| 4,939,368 A | 7/1990 | Brown | |
| 5,175,774 A * | 12/1992 | Truax | B44B 7/00 235/456 |
| 6,280,655 B1 * | 8/2001 | Xu | C09K 11/643 252/301.4 R |
| 6,431,007 B1 | 8/2002 | Roy | |
| 6,934,013 B2 * | 8/2005 | Vachon | G01B 11/16 356/32 |
| 7,127,950 B2 * | 10/2006 | Fonov | G01L 1/24 73/762 |
| 7,157,726 B2 * | 1/2007 | Naruoka | G01B 11/028 250/559.19 |
| 7,344,498 B1 * | 3/2008 | Doughty | A61B 5/0059 600/306 |
| 7,377,181 B2 | 5/2008 | Christ, Jr. et al. | |
| 7,408,297 B2 * | 8/2008 | Xu | H01L 41/08 313/508 |
| 7,779,707 B2 | 8/2010 | Shih et al. | |
| 8,017,174 B2 * | 9/2011 | Meiring | G06K 7/14 427/2.11 |
| 8,245,578 B2 * | 8/2012 | Ranson | G06K 19/06037 73/760 |
| 8,250,927 B2 * | 8/2012 | Anand | G01B 7/18 73/763 |
| 8,347,727 B2 * | 1/2013 | Hovis | G06K 19/06037 73/760 |
| 8,366,011 B2 * | 2/2013 | Hovis | G06K 19/06037 235/462.01 |
| 8,600,147 B2 * | 12/2013 | Iliopoulos | G01B 11/165 356/32 |
| 8,827,973 B2 * | 9/2014 | Stokes | A61M 1/0001 604/319 |
| 9,228,859 B2 * | 1/2016 | Ranky | H01L 41/314 |
| 9,311,566 B2 * | 4/2016 | Iliopoulos | G06K 9/6232 |
| 9,372,128 B1 * | 6/2016 | Kneezel | G01L 1/241 |
| 9,459,163 B2 * | 10/2016 | Sirbuly | G01L 1/242 |
| 9,551,620 B2 * | 1/2017 | Singh | F01D 17/02 |
| 2007/0059468 A1 | 3/2007 | Kirkegaard et al. | |
| 2012/0250001 A1 | 10/2012 | Tanaka | |
| 2015/0362669 A1 * | 12/2015 | Aizenberg | G01L 1/247 385/13 |
| 2016/0290880 A1 * | 10/2016 | Lewis | G01L 1/2287 |

FOREIGN PATENT DOCUMENTS

| | | |
|---|---|---|
| JP | S6128808 A | 2/1986 |
| WO | 2007096705 A2 | 8/2007 |
| WO | 2008090495 A1 | 7/2008 |

* cited by examiner

NON-CONTACT METHOD FOR MEASUREMENT OF STRAIN PROFILE AT A LOCATION INTERPOSED WITHIN A SOFT DEFORMABLE OBJECT WITH DYNAMIC EVOLUTION OF THE STRAIN UNDER DYNAMIC LOADING OR FRACTURE OF THE OBJECT

CROSS-REFERENCE TO RELATED APPLICATIONS

This application is the United States national phase of International Application No. PCT/IN2014/000283 filed Apr. 28, 2014, and claims priority to Indian Patent Application No. 1305/DEL/2013 filed May 3, 2013, the disclosures of which are hereby incorporated in their entirety by reference.

BACKGROUND OF THE INVENTION

Field of the Invention

The invention generally relates to the technical field of deformation and fracture of soft deformable objects for example crosslinked hydrogel, elastomers. In particular, the invention relates to estimating displacement and strain profile at a location interposed within a soft deformable object. More particularly, the invention relates to a non-contact method for measurement of strain profile at a location interposed within a soft deformable object with dynamic evolution of the strain under dynamic loading or fracture of the object.

Description of Related Art

The soft deformable objects are known to have a large number of applications, which normally deform following simple linear elastic laws or deform exhibiting more complex rheological behavior. The material may be homogeneous or heterogeneous so that the rheological properties may remain uniform or vary spatially. The material may undergo large deformation to the extent that it can undergo fracture.

Determination of deformation and strain profile inside a soft object and the dynamic evolution of these quantities, during external loading, fracture with an intruding object and deformation due to variety of internal processes are important for large number of engineering and biomedical applications. Several non-contact optical methods are known which essentially involve the use of tracer particles randomly spread or arranged in an orderly manner in the form of a rectangular grid on the surface of the object. Deformation of the object results in displacement of these particles which is visualized optically and recorded using a video camera fitted with a microscope. In many cases, instead of the tracer particles one can use a thin transparent film which results in interference fringes when illuminated by light. The interference pattern changes on application of load on the object which is captured optically and analyzed using an image-processing software for estimation of displacement including the strain field. Notably, all these known methods are suitable for estimating strain on the surface of a body. However, many situations, for example fracture of a soft body driven by an intruding object, demands estimation of the strain field inside the body, especially that at the closest vicinity of the crack tip. Such knowledge is important for understanding a local fracture strength of the material, for driving a propagating crack along a superior materials with enhanced failure strength and so on. There is actually no known method for experimental determination of the strain value or strain profile within bulk-material or over a large volume of the material. It is in this context that we have presented here the idea of embedding a tracer grid consisting of fine lines or uniformly spaced dots on a single plane embedded inside the soft deformable body. We can then subject it to external or internal tensile/compressive shear stress, or fracture it by driving an intruder through it. The deformation of this grid in response to the load provides us the estimation of the displacement and strain profile of the material at that location. We have presented below a brief description of patents closely related to the subject of the current problem.

Patent number EP 0783837 B1 describes a method and an apparatus for joining successive blocks of kneaded dough in order to produce a continuous sheet of dough. The essence of the cited invention resides in mechanical mixing of several pieces of dough without any chemical interaction.

Patent number EP 1281070 A1 teaches methods, apparatus and kits for integrally labeling polymeric gels, such as polyacrylamide and agarose gels, with indicia written on a polymeric material which bonds to the gel matrix as the gel polymerizes. The gels are used for electrophoretic analysis of biological molecules like DNA, RNA and proteins.

International patent application published under WO 2008090495A1 describes a contact-less optical method of measuring strain on a skin surface when a person is shaving. In essence, the skin of a human being is known to have a pattern and which is imaged using a digital camera both in unstrained and strained conditions. The deflection of the skin is estimated by measuring deflection of the pattern.

U.S. Pat. No. 6,431,007 describes a non-contact strain measuring method in which reference lines are drawn on the surface of low modulus porous material by using a fluorescent ink as the dye. The specimen is then viewed under an optical microscope both in loaded and unloaded conditions. The Poisson's ratio is calculated from the strain measurements in two orthogonal directions.

U.S. Pat. No. 4,781,455 describes a method and an apparatus for measurement of strain by optical technique. In essence, a thin transparent film of thickness 3-20 µm is adhered on the surface of an object. A beam of light produces interference pattern when projected onto the object because of superimposition of reflected and transmitted light at the boundary surface of the film. The interference pattern alters depending on loading on the film which is analyzed and measured by using an image processing software.

U.S. Pat. No. 7,377,181 describes a method of measuring strain in which a dot pattern is made on the surface of a test specimen. During loading and unloading of the specimen, the separated distance between two dots changes which is measured and used for estimating the strain.

U.S. Pat. No. 4,939,368 describes a method and apparatus for measuring strain of an object, the surface of which is provided with a diffraction grating. The grating is illuminated with radiation including at least two frequencies to produce an interference pattern. At least a portion of the interference pattern corresponding to at least one of the frequencies is detected and analyzed to determine the strain.

U.S. Pat. No. 7,779,707 describes a Piezoelectric Finger Sensor that acts as an "electronic finger" capable of accurately and non-destructively measuring both the Young's compression modulus and shear modulus of tissues with, gentle touches to the surface. The PEFS measures both the Young's compression modulus and shear modulus variations in tissue generating a less than one-millimeter spatial resolution up to a depth of several centimeters. This offers great potential for in-vivo early detection of diseases. A portable hand-held device, is also disclosed. The PEF offers superior sensitivity.

SUMMARY OF THE INVENTION

Accordingly, there is provided A non-invasive method for estimation of strain profile and dynamic evolution of the strain at a location interposed inside a block of soft material, comprising: forming a tracer grid consisting of microscopic lines or regularly spaced microscopic dots on a single plane buried inside the soft block; preparation of a deformable object embedded with the tracer grid in three primary steps: i. preparing a block of crosslinked material by crosslinking a first predetermined quantity of a pre-polymer solution containing a monomer, a crosslinking agent, and an initiator and promoter all mixed in a solvent at a known stoichiometric weight ratio, the crosslinking reaction being carried out inside a mold at room temperature or at an elevated temperature, such that a block of the crosslinked material having one of a flat face and a desired curvature; ii. transferring a grid comprising of lines or dots onto the face by direct writing or transferring from an easy release surface; and iii. crosslinking a second predetermined quantity of the same pre-polymer solution on the gel surface, such that this second corsslinked material gets welded to the first one forming a monolithic block having a plane containing tracer particles embedded inside. Visualizing and recording the displacement of the tracer grid when the composite block is subjected to normal, shear or torsional loading or fracture by insertion of an object. The strain field is estimated from the data of displacement of the tracer grid.

One aspect of the inventive method is generation of a tracer grid at a plane embedded within the object. Loading the object externally or internally leads to deformation of the grid which is visualized and video recorded using a suitable camera. The tracer grid is embedded via following sequence of steps namely, one portion of the deformable object is prepared by crosslinking a pre-polymer solution; tracer particles or dots or tracer lines are transferred on one face of it. This face of the gel, which can be flat or curved as desired, is used as a substrate on which, another portion of the same prepolymer solution is crosslinked. During this process, the newly formed block of the crosslinked material gets chemically bonded and welded to the substrate leading to a monolithic block with an embedded array of particles on a plane interposed within the composite block. The usefulness of this embedded tracer grid has been demonstrated by carrying out several experiments. For example, a fracture was made on the block by inserting a blunt or sharp object through the plane in which the tracer plane is embedded. The strain profile and its dynamic evolution in the vicinity of the crack have been estimated by following the displacement of the tracer grid. In another embodiment of the invention, the plane containing tracer grid was embedded inside a gel cylinder such that it remained concentric with the outer curved surface of the cylinder. When the cylinder was subjected to torsion, the rotational shear strain at the location of the tracer plane could be estimated by measuring the displacement of the tracer grid. In another embodiment of the invention, the tracer grid was embedded inside a soft indenter as a horizontal plane at the vicinity of its tip.

DETAILED DESCRIPTION OF THE INVENTION

Admittedly, acquiring the information about strain field over the surface of a deformable object, using tracer dot or particles is well known. The present invention however provides a process to quantify experimentally using tracer particles, the dynamic evolution of a strain field at a location interposed within the bulk of a soft solid when it is loaded externally or during fracture. Thus, the present invention is developed through combination of the concept of welding two blocks of the same crosslinkable material like hydrogel without use of any second material, and placing a tracer grid on the surface of the crosslinkable material. The hydrogel being optically transparent, it allows visualization and recordal of displacement of the tracer particles accurately with the help of a video camera. The inventive process was validated by creating a fracture on such a block of gel using a blunt object for example, a flat punch, and sharp objects for example, hypodermic syringe needles having either a single tip or closely spaced multiple tips. These experiments have shown that strain profile in the material evolves differently in these different situations, thus signifying that the invented method may be an important tool for carrying out material research in variety of engineering and biomedical applications. In another aspect of the invention, a soft indenter embedded with the tracer gird is produced for estimating the softness or hardness of a substrate. Although, the invention uses an optically transparent material to demonstrate the possible applications, with the use of an infrared camera, it will be possible also to monitor displacement of the tracer particles interposed within a opaque object.

Figure 1:
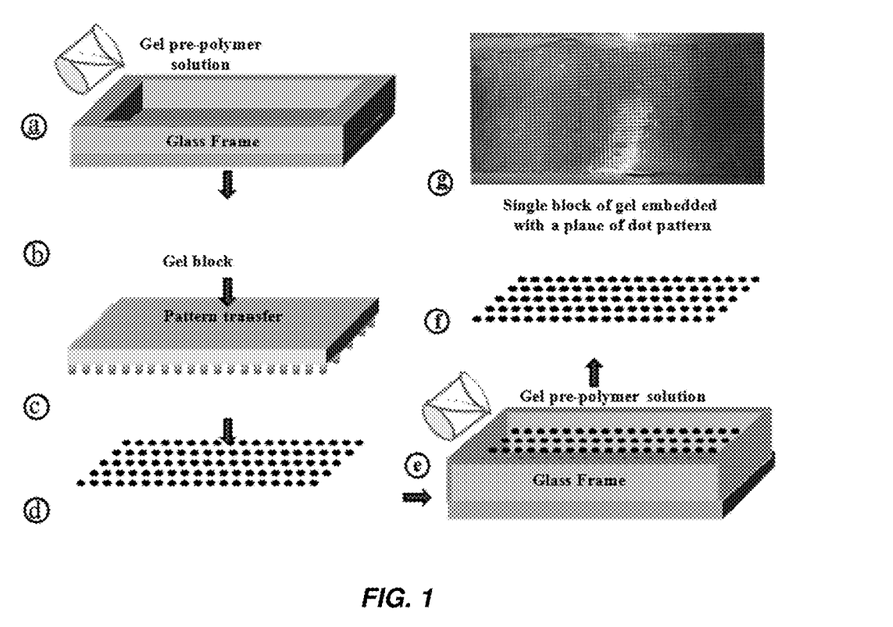
FIG. 1 Shows a process of preparing a block of gel embedded with a plane containing tracer grid.
Figure 2:
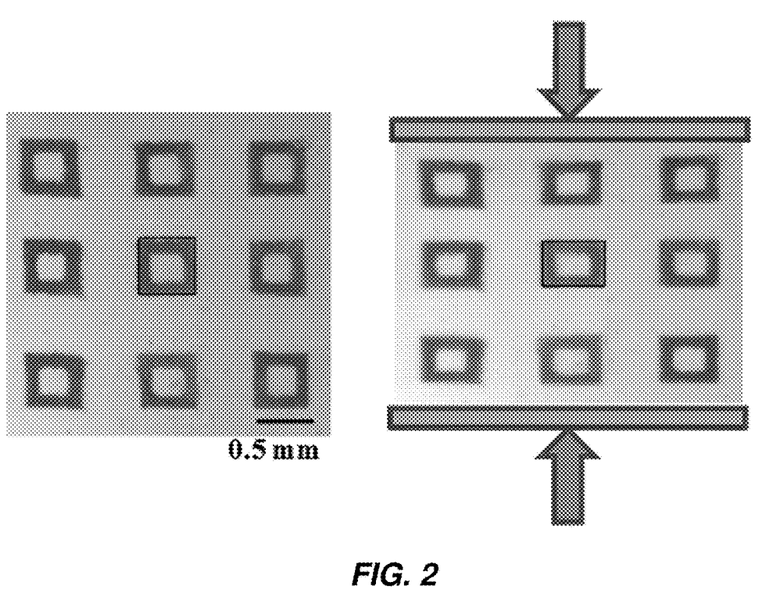
FIG. 2 Shows the result of uniaxial compression of the embedded gel block.
Figure 3:
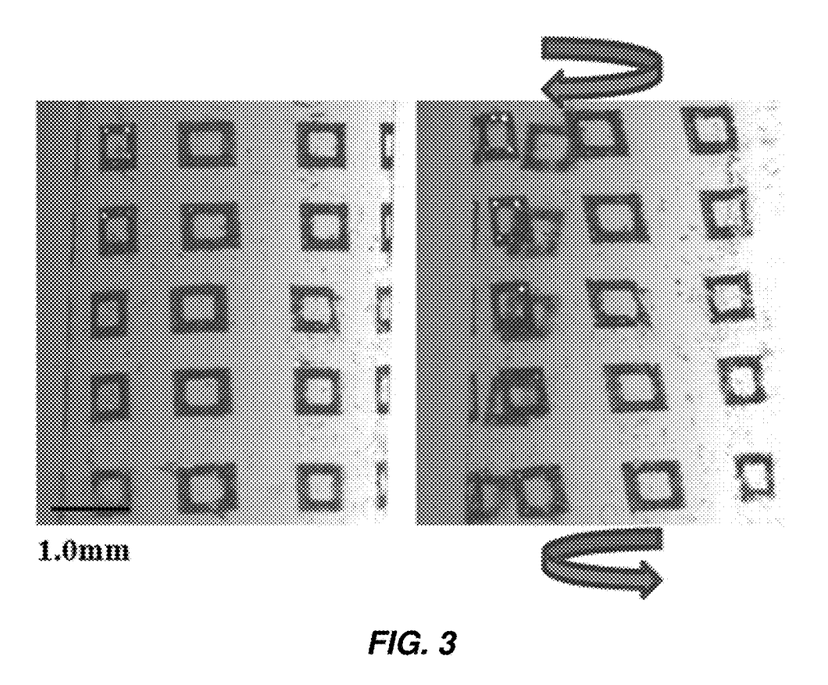
FIG. 3 Shows a cylindrical block of gel in which the tracer grid is embedded on a curved plane.

FIG. 1 shows the sequence of steps depicting the method of preparing a block of gel embedded with a plane containing tracer grid. FIG. 2 establishes that an uniaxial compression of the gel block embedded with tracer grid can result in Poisson ratio and Young's modulus of the material of the gel. FIG. 3 shows that a tracer grid is embedded on a curved plane at the bulk of a cylindrical block of gel. Torsion of the cylinder about its axis can yield torsional modulus of the gel material.

Figure 4:
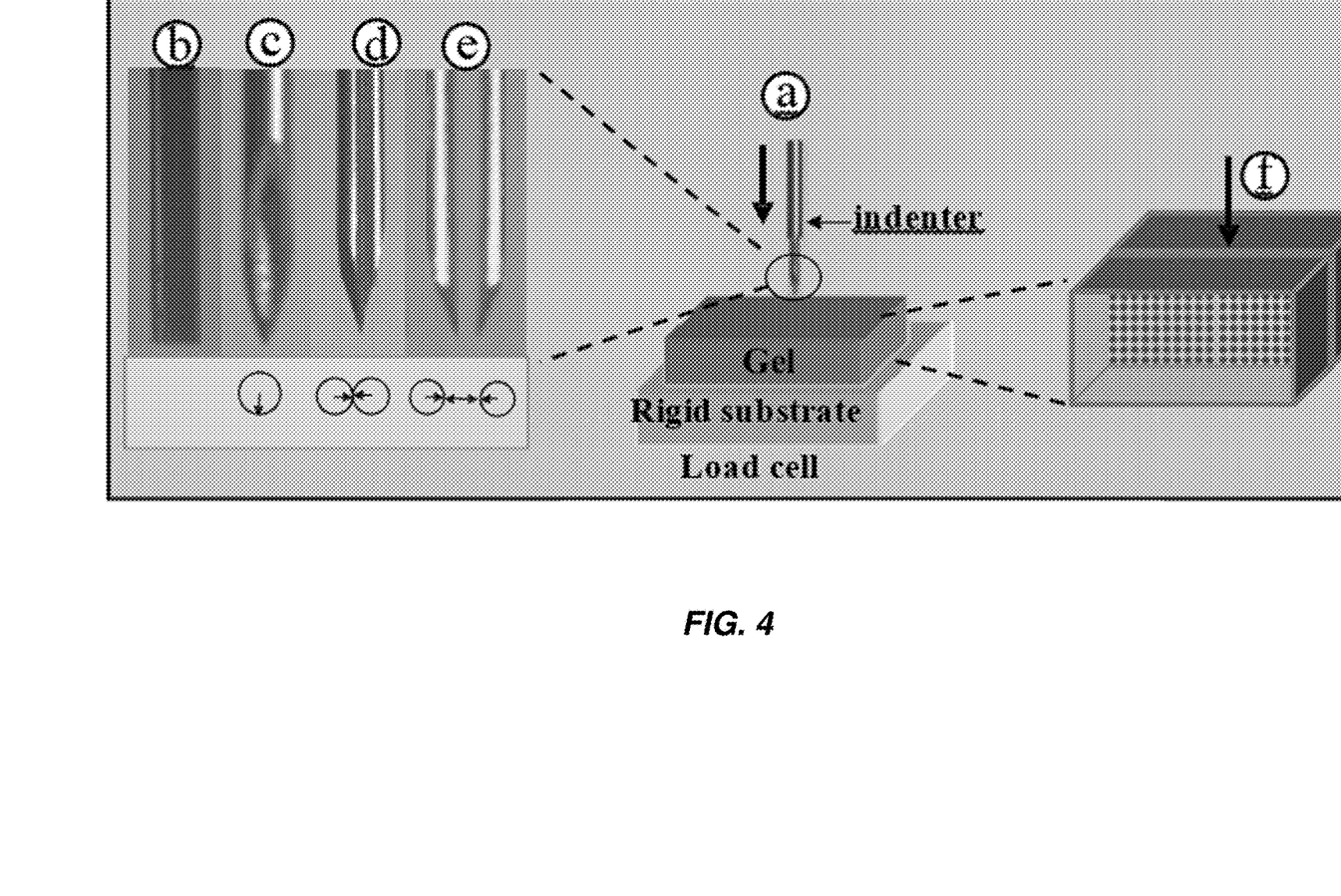
FIG. 4 Shows an experimental concept of punching a block of gel with syringe needle.

FIG. 4 shows a schematic of a typical experiment. (a) An indenter, e.g. a flat bottom punch or a syringe needle is driven vertically down at a uniform speed into the gel block bonded to a rigid substrate, such that the indenter drives through the plane of tracer grid and it remains oriented symmetric to this plane. The optical micrographs of typical single and double needles are shown in (b)-(d). (e) Schematic of a typical sample of gel embedded with the plane of dot pattern. The needle is driven into the gel such that it remains symmetric to this plane.

Figure 5:
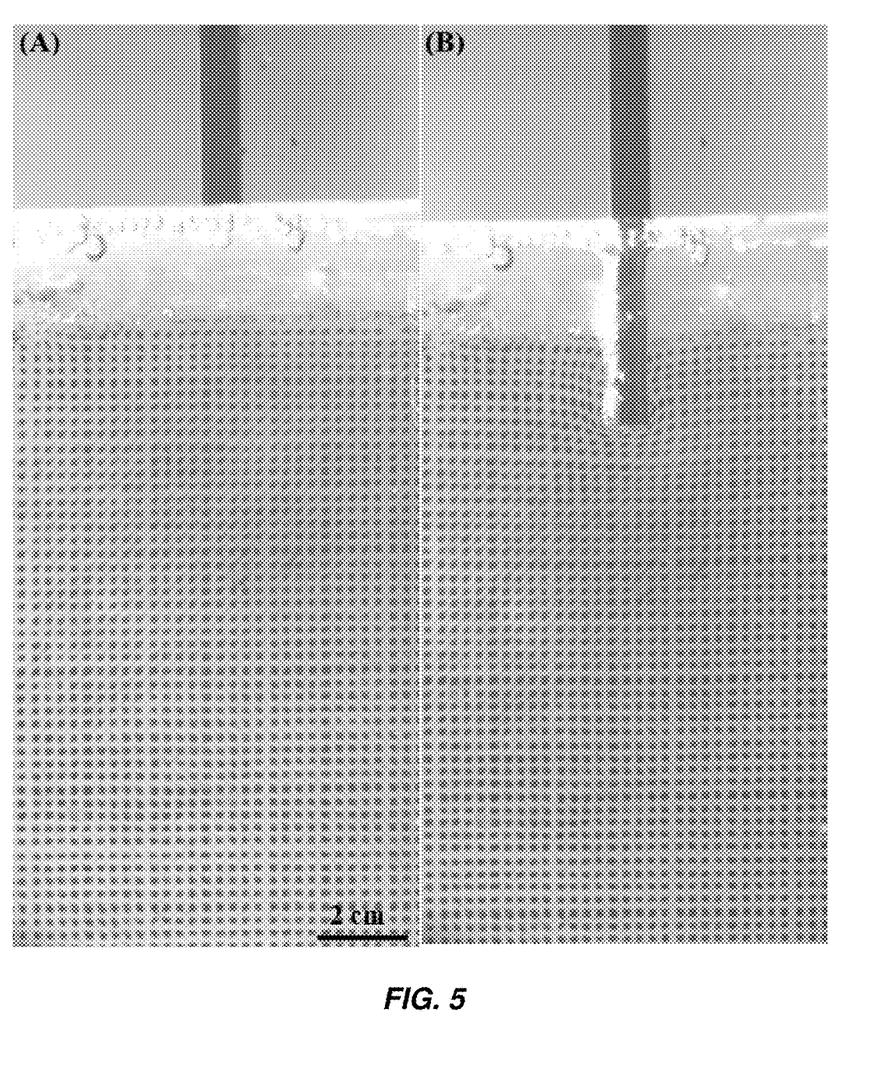
FIG. 5 Shows a flat punch driven into a cross-linked block of gel.

FIG. 5 shows that a flat punch is driven into a crosslinked block of polyacrylamide gel through the plane in which the tracer grid remains embedded. Images A and B show the displacement of the grid because of progress in the fracture.

Figure 6:
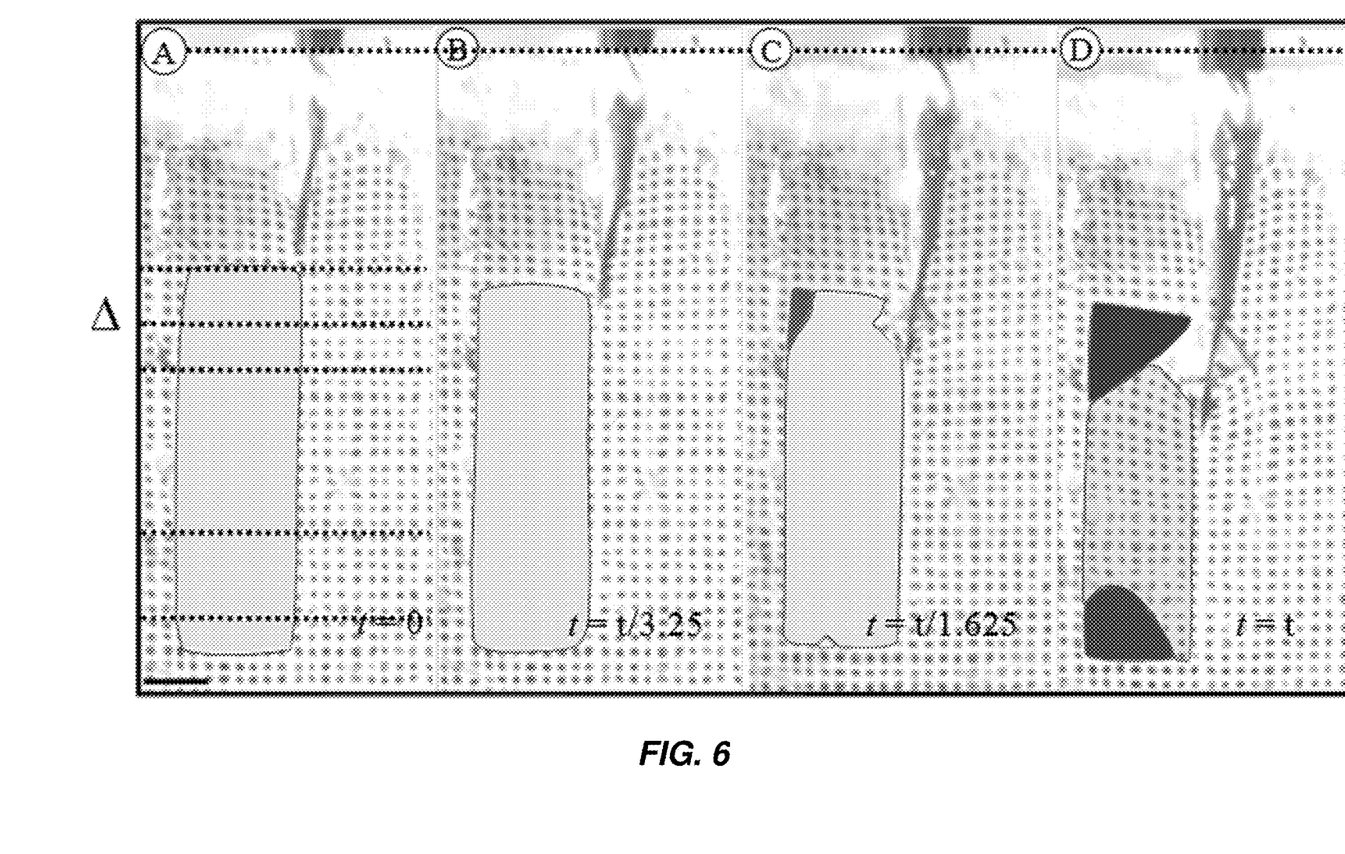
FIG. 6 Shows a video images depicting the progress of fracture when a block of gel is punctured.

FIG. 6 depicts a sequence of video micrograph which interalia shows the progress of the fracture when a block of gel of modules $\mu=30$ kPa is punctured with a single tip needle of diameter d=1.2 mm. Optical image A to D represent time 0, 2, 4 and 6.5 sec respectively. The regions represent respectively the zones of tensile and compressive vertical strains, $e_{yy}$. The dotted line represents the undeformed gel surface. The scale bar represents 1.2 mm.

Figure 7:
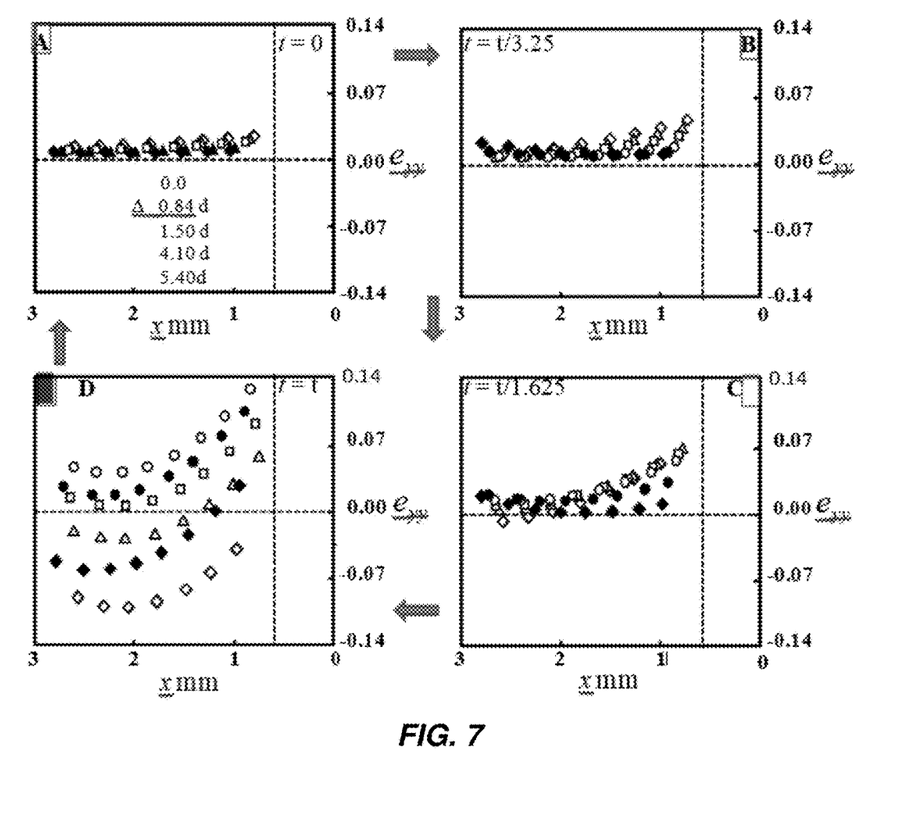
FIG. 7 Shows a graph depicting normal strain as a function of distance from underformed surface of the gel.

FIG. 7 shows Plots a-d representing normal strain $e_{yy}$ as a function of distance x from the central axis of the needle, also with respect to vertical distance from underformed surface of the gel. Symbols: ◇,△,□,○,●and ◆ represent respectively 4.07, 5.08, 5.82, 7.41, 8.97 and 10.54 mm from the underformed gel surface. Scale bar represents 1.2 mm.

Figure 8:
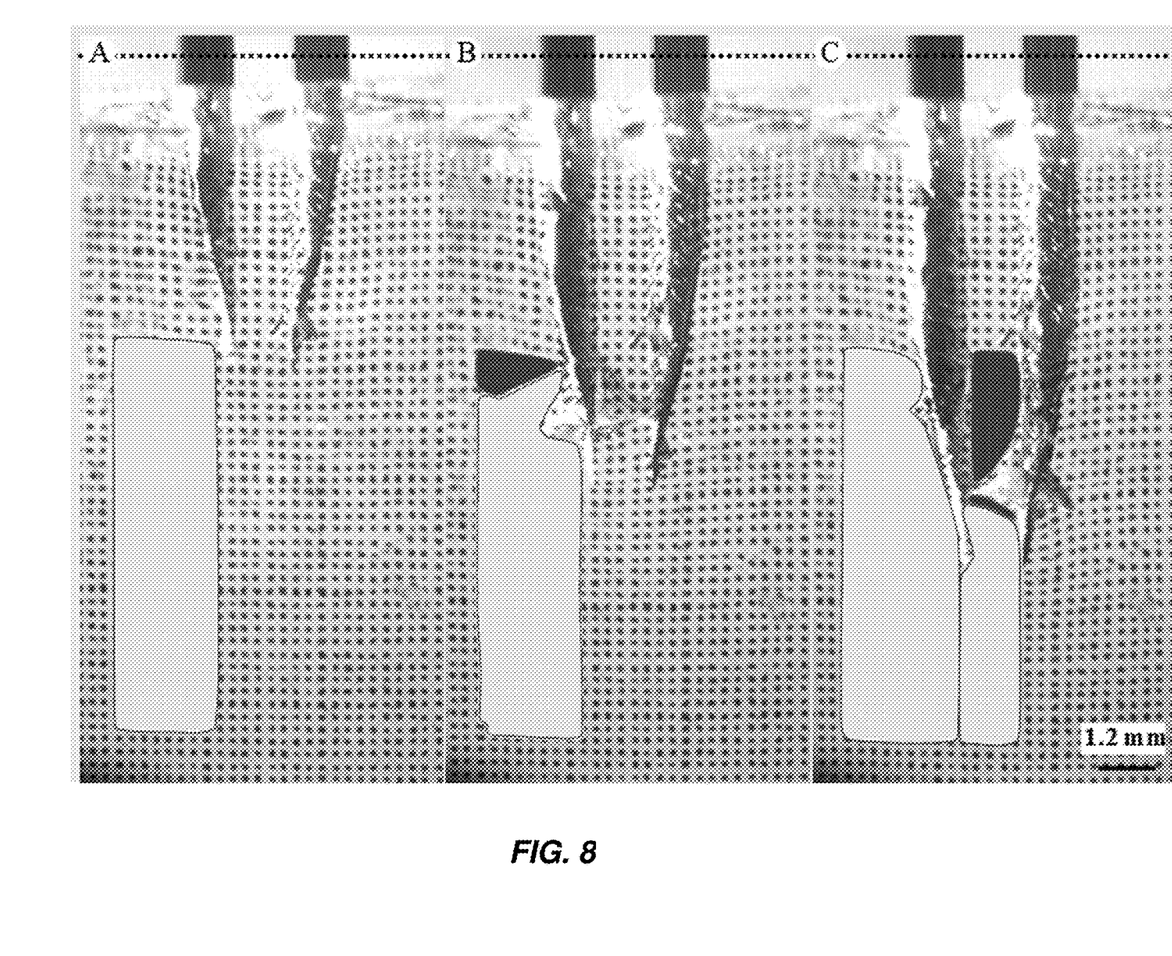
FIG. 8 Shows optical micrograph depicting evolution of regions of tensile and compressive strain in the gel.

FIG. 8 is a sequence of the optical micrograph showing evolution of regions of tensile and compressive strain $e_{yy}$ in the gel, when a double tip needle with constituent tip diameter d=1.2 mm and inter-tip gap δ=1.2 mm is used for puncturing a block of gel of modulus $\mu=30$ kPa. Green and yellow color signify, respectively, zones of tensile and compressive vertical strain. Optical micrographs A to C represent the strain profile at time 0.0, 5.0 and 8.25 sec respectively.

Figure 9:
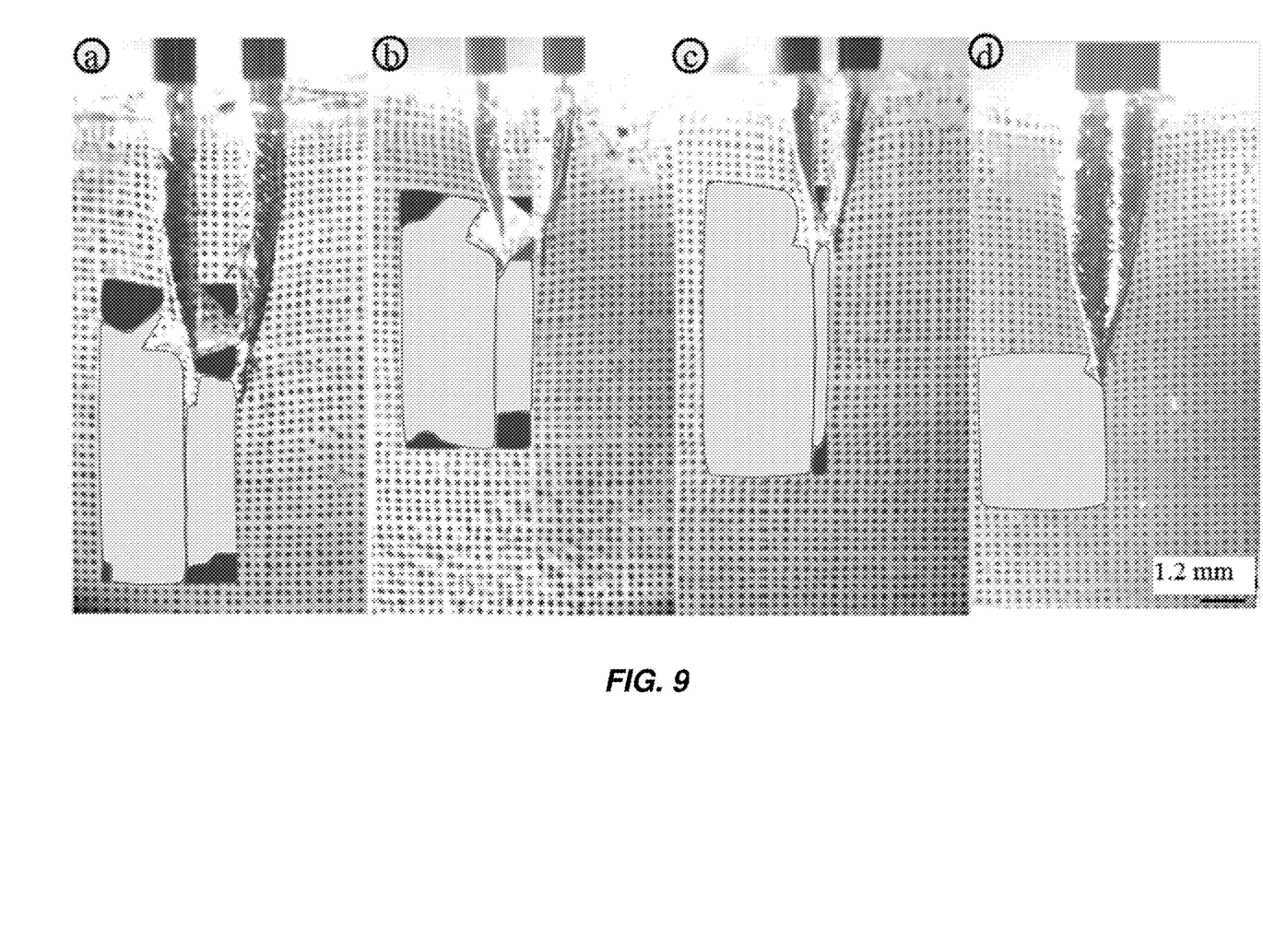
FIG. 9 Optical image showing profile of punching a block of gel.

Optical image of FIG. 9 shows $e_{yy}$ profile of puncturing of a block of gel (modulus $\mu=30$ kPa) by a double tip needle with systematically varied gap. A-d denotes δ=1.2, 0.92, 0.45 and 0.0 mm respectively.

Figure 10:
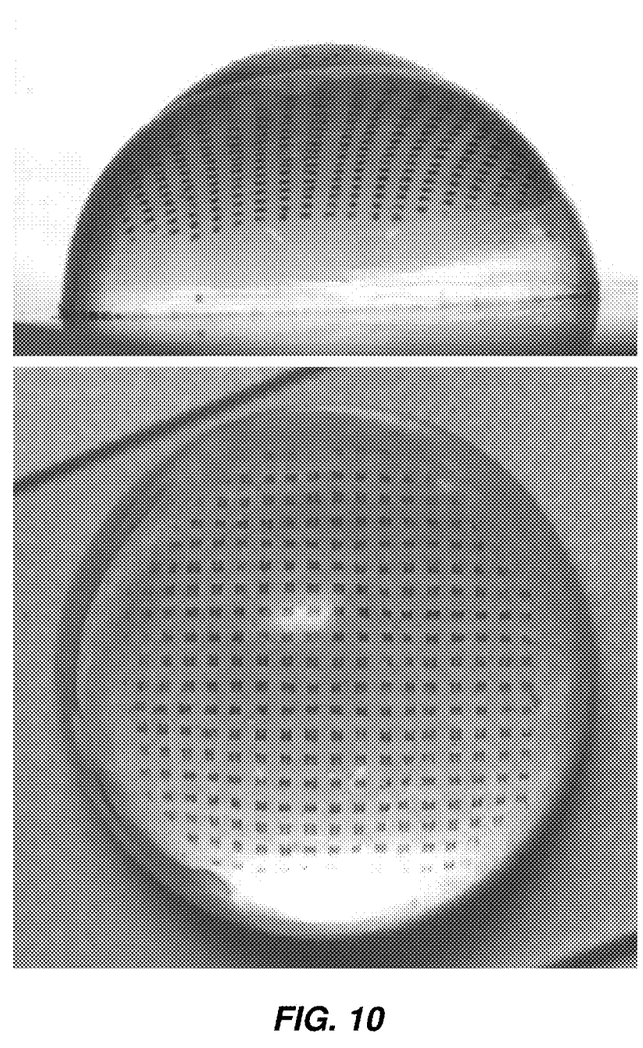
FIG. 10 Shows the top and side views of a hemispherical indenter with an embedded plane of tracer grid.

Optical image of FIG. 10 shows the top and side views of a hemispherical indenter with an embedded plane of tracer grid.

ADVANTAGES OF THE INVENTION

1. In contrast to all conventional methods of obtaining strain of a body, the idea of obtaining deformation and strain profile at a location buried inside a deformable object is a novel idea.
2. The idea of obtaining the dynamic evolution of different components of strain at the vicinity of the crack tip inside the body is a novel idea.
3. The idea of embedding an array of tracer particles in the form of a grid or uniformly spaced dots on a plane which can be embedded inside the body is a novel idea.
4. The idea of welding of two separate bodies of the same crosslinkable material without use of any second material as glue is a novel idea.
5. The ideal of welding of two separate bodies of the same crosslinkable material for embedding a plane containing the grid of tracer dots or lines is a novel idea.
6. The idea of creating gel layer consisting of multiple layers of different modulus via successive welding of layers is a novel idea.
7. The idea of carrying out fracture of the soft gel through the said plane in order to visualize and measure the displacement of the tracer particles is a novel idea.
8. The idea of developing tests by using the said gel blocks embedded with a plane of tracer particles as model material for studying fracture of similar soft objects is a novel idea.
9. The idea of developing tests for examining the effect of closely spaced cracks driven by multiple objects on the strain field inside a crosslinkable material is a novel idea.

FUTURE APPLICATIONS

1. For designing get based optical load sensor for measuring very small loads
2. For designing indenters embedded with a tracer grid for variety of applications, e.g. measuring local modulus of a substrate
3. Safety valves and optical switches
4. For gel labeling useful for gel electrophoresis purposes
5. For preparing gel block with discontinuously varying pore sizes and other properties for gel electrophoresis purposes.

We claim:
1. A non-invasive method for estimation of strain profile and dynamic evolution of the strain at a location interposed inside a block of material, comprising:
   preparing a first block of crosslinked material by crosslinking a first predetermined quantity of a pre-polymer solution containing a monomer, a crosslinking agent, an initiator, and a promoter in a solvent at a known stoichiometric weight ratio, the crosslinking reaction being carried out inside a mold at room temperature or at an elevated temperature, such that the first block of the crosslinked material has one of a flat face and a desired curvature;
   transferring a tracer grid comprising of tracer particles in a form of lines or dots onto a surface of the first block by direct writing or transferring;
   preparing a second block of crosslinked material by crosslinking the pre-polymer solution containing a monomer, a crosslinking agent, an initiator, and a promoter in a solvent at a known stoichiometric weight ratio on the surface of the first block to form a composite block comprising the second block of crosslinked material in contact with the surface of the first block and a plane containing the tracer particles is embedded between the first block and the second block;
   visualizing and recording displacement of the tracer grid when the composite block is subjected to normal shear, torsional loading, or fracture by insertion of an object therein; and
   estimating a strain field from the displacement of the tracer grid.
2. The method as claimed in claim 1, wherein the block of material is optically transparent or opaque.
3. The method as claimed in claim 1, wherein the tracer grid comprises at least one of an ink, a fluorescent dye, microscopic particles, quantum dots, and single or multi-walled carbon nanotubes.
4. The method as claimed in claim 1, wherein the tracer grid is embedded on a flat or a curved surface.
5. The method as claimed in claim 1, further comprising using an indenter to estimate softness of a fragile material.
6. The method as claimed in claim 1, comprising estimating a dynamic evolution of the strain field.
7. The method as claimed in claim 1, further comprising estimating a change in the strain field using inclusions inside the object.
8. The method as claimed in claim 1, further comprising estimating a Poisson ratio of the block of material.

9. The method as claimed in claim 1, wherein the cross-linked material comprises several layers of material having similar or dissimilar rheological properties.

* * * * *